(12) United States Patent
Regner et al.

(10) Patent No.: US 8,778,311 B2
(45) Date of Patent: Jul. 15, 2014

(54) ORAL ZINC COMPOSITIONS

(75) Inventors: Meinrad Regner, Mainz (DE); Maurice Joseph Prendergast, Bracknell (GB); Owen Thurlby, Byfleet (GB)

(73) Assignee: The Procter & Gamble Company, Cincinnati, OH (US)

( * ) Notice: Subject to any disclaimer, the term of this patent is extended or adjusted under 35 U.S.C. 154(b) by 818 days.

(21) Appl. No.: 11/725,835

(22) Filed: Mar. 20, 2007

(65) Prior Publication Data
US 2007/0224134 A1    Sep. 27, 2007

(30) Foreign Application Priority Data

Mar. 22, 2006 (EP) .................................. 06005851

(51) Int. Cl.
*A61K 8/27* (2006.01)

(52) U.S. Cl.
USPC ............. 424/49; 424/643; 424/715; 424/716; 424/717; 424/727

(58) Field of Classification Search
USPC .................... 424/49, 643, 715, 716, 717, 727
See application file for complete search history.

(56) References Cited

U.S. PATENT DOCUMENTS

| | | | |
|---|---|---|---|
| 3,802,441 A * | 4/1974 | Hammersmith | 131/343 |
| 4,022,880 A | 5/1977 | Vinson et al. | |
| 4,082,841 A | 4/1978 | Pader | |
| 4,100,269 A | 7/1978 | Pader | |
| 4,138,477 A | 2/1979 | Gaffar | |
| 4,144,323 A | 3/1979 | Lamberti | |
| 4,154,815 A | 5/1979 | Pader | |
| 4,160,054 A | 7/1979 | Wagenknecht et al. | |
| 4,289,755 A | 9/1981 | Dhabhar | |
| 4,325,939 A | 4/1982 | Shah | |
| 4,339,432 A | 7/1982 | Ritchey et al. | |
| 4,416,867 A | 11/1983 | Ritchey et al. | |
| 4,425,325 A | 1/1984 | Ritchey et al. | |
| 4,469,674 A | 9/1984 | Shah et al. | |
| 4,522,806 A | 6/1985 | Muhlemann et al. | |
| 4,568,540 A | 2/1986 | Asano et al. | |
| 4,647,452 A | 3/1987 | Ritchey et al. | |
| 4,664,906 A | 5/1987 | Sipos | |
| 4,814,163 A | 3/1989 | Barth | |
| 4,814,164 A | 3/1989 | Barth et al. | |
| 4,992,259 A | 2/1991 | Schiraldi et al. | |
| 5,000,944 A | 3/1991 | Prencipe et al. | |
| 5,085,850 A | 2/1992 | Pan et al. | |
| 5,188,820 A | 2/1993 | Cummins et al. | |
| 5,326,554 A * | 7/1994 | Fitz, Jr. | 424/49 |
| 5,330,748 A * | 7/1994 | Winston et al. | 424/49 |
| 5,385,727 A | 1/1995 | Winston et al. | |
| 5,455,024 A * | 10/1995 | Winston et al. | 424/52 |
| 5,456,902 A | 10/1995 | Williams et al. | |
| 5,587,147 A | 12/1996 | Domke et al. | |
| 5,624,906 A * | 4/1997 | Vermeer | 514/23 |
| 5,714,447 A | 2/1998 | Jones et al. | |
| 5,855,873 A | 1/1999 | Yam | |
| 6,015,547 A * | 1/2000 | Yam | 424/49 |
| 6,592,849 B2 | 7/2003 | Robinson et al. | |
| 6,706,256 B2 * | 3/2004 | Lawlor | 424/58 |
| 6,723,305 B2 | 4/2004 | DePierro et al. | |
| 2003/0202945 A1 | 10/2003 | Ryles et al. | |

FOREIGN PATENT DOCUMENTS

| | | |
|---|---|---|
| EP | 1072253 | 1/2001 |
| EP | 1586312 | 10/2005 |
| WO | WO 94/14406 | 7/1994 |
| WO | WO 94/14407 | 7/1994 |
| WO | WO 94/26244 | * 11/1994 |
| WO | WO 94/26245 | 11/1994 |
| WO | WO 95/34274 | 12/1995 |
| WO | WO 96/25913 | 8/1996 |
| WO | WO 96/37183 | 11/1996 |
| WO | WO 98/37859 | 11/1996 |
| WO | WO 99/20238 | 4/1999 |
| WO | WO 00/28952 | 5/2000 |
| WO | WO 00/61092 | 10/2000 |
| WO | WO 02/02060 | 1/2002 |
| WO | WO 2004/024112 | 3/2004 |
| WO | WO 2004/045594 | 6/2004 |

OTHER PUBLICATIONS

Price et al., The pH of Tooth-Whitening Products, 2000, J Can Dent Assc, vol. 66, pp. 421-426.*
U.S. Appl. No. 11/635,590, filed Dec. 12, 2006, Glandorf, et al.

* cited by examiner

*Primary Examiner* — Ali Soroush
(74) *Attorney, Agent, or Firm* — Armina E. Stricklin

(57) ABSTRACT

The present invention relates to an oral composition comprising, in an orally acceptable carrier, from about 0.1% to about 5% zinc oxide; and from about 0.1% to about 5% of a source of carbonate ions selected from alkali metal and ammonium carbonates and bicarbonates. The molar ratio of carbonate ion to zinc ion is from about 0.05:1 to about 1:1. The composition has good antiplaque efficacy and taste. Preferred compositions are toothpastes.

10 Claims, No Drawings

ORAL ZINC COMPOSITIONS

FIELD OF THE INVENTION

The present invention relates to oral compositions comprising zinc oxide as an anti-plaque agent.

BACKGROUND OF THE INVENTION

The incorporation of zinc compounds into oral care products to provide anti-plaque effects, deriving from the antimicrobial properties of the zinc, is well known in the prior art. Also well known is the astringency of such compounds, which produces an unpleasant taste in the mouth and is an inhibition to their use in mass appeal products. This also imposes some restrictions on the flavours that can successfully be used in a zinc containing oral composition.

It has previously been recognised that the more soluble zinc salts, such as zinc chloride and zinc nitrate generally give rise to a worse taste than the less soluble zinc salts, such as zinc oxide and zinc citrate dihydrate. It has also been generally believed that the zinc needs to be in soluble form to be efficacious against bacteria and plaque. There is therefore a trade-off to be made between efficacy and taste. Many attempts have been made, and described in the patent literature, to reduce the astringency of zinc in oral compositions, especially dentifrice compositions. A non-exhaustive list includes the following disclosures.

WO 94/14406 and WO 94/14407 describe formulating a source of zinc ions, preferably zinc oxide or zinc nitrate, along with sources of citrate and pyrophosphate ions in defined ratios.

WO 94/26244 and WO 94/26245 report surprising anti-plaque effectiveness from oral care compositions comprising insoluble zinc oxide, even from compositions having a pH of about 7.5-9.5 through the addition of sodium bicarbonate. The compositions are also absent the metallic and astringent taste of zinc. WO 94/26244 hypothesises that the anti-plaque activity arises through the release of zinc ions by the acidic action of plaque acids on zinc oxide trapped in the plaque.

WO 95/34274, acknowledging the teaching of WO 94/26244, goes further and discloses that sodium bicarbonate itself reduces the astringency of zinc species other than the oxide, such as zinc citrate or zinc chloride.

WO 96/25913 describes the preparation of monophasic zinc hydroxycarbonate from the reaction of a soluble zinc salt with an alkali metal carbonate. WO 96/25913 further discloses that zinc hydroxycarbonate shows synergistic antimicrobial activity in toothpastes with abrasive agents and that lactic acid generated in the mouth triggers the release of zinc ions.

WO 96/37183 discloses that a combination of a humectant and a salt, such as the chloride, carbonate or bicarbonate of sodium or potassium, can mask astringent tastes, such as those of zinc chloride, zinc salicylate, zinc gluconate, silver nitrate, and silver gluconate.

WO 98/37859 also advises the salt approach, teaching that sodium or ammonium chloride as well as alkali, alkaline earth or ammonium carbonates mask the taste of easily soluble zinc salts, especially the chloride, sulfate, lactate and acetate.

A different approach is offered by WO 99/20238, whose invention employs a nonionic polymer to mask the astringency of zinc chloride, sulfate, citrate, acetate and thiocyanate.

The invention of WO 00/28952 is to mask the undesirable taste of an ionisable zinc compound, such as the oxide, citrate, chloride, acetate, hydroxide, fluorosilicate, fluorozirconate, acetate, gluconate with a synergistic flavouring combination of a flavouring oil and lauryl alcohol.

EP 1 072 253 A1 reports that the astringency of zinc oxide is reduced by decreasing its particle size and thereby increasing its surface area, a further taste enhancement is obtained by combining it with Palatinit (isomalt).

US 2003/0202945 uses a physical approach to the zinc taste problem, incorporating its zinc salts, especially zinc citrate dihydrate, into its oral products in the form of relatively large beads.

Whilst the foregoing disclosures primarily aim to mask the taste of zinc, WO 00/61092 increases the bioavailability of zinc in a dentifrice, thereby enabling a reduction in the amount, by buffering the dentifrice at a pH of from 3 to 5.5.

Despite all of the foregoing, further improvements are needed in the formulation of zinc into oral compositions, in order to deliver the combination of anti-plaque efficacy with acceptable taste.

It has now surprisingly been found that carbonate ions appear to potentiate the action of zinc but that the best aesthetics are obtained when the level of carbonate is relatively low compared to the zinc. Without wishing to be bound by theory it is believed that the carbonate ion acts to make the zinc ion bioavailable in terms of its anti-plaque efficacy, releasing it as necessary and drawing upon the insoluble zinc oxide as reservoir of potential zinc ions. This is somewhat surprising given that zinc carbonate itself is relatively insoluble. It has been found by the present inventors that if too much carbonate is used the taste of the product is affected and the zinc taste becomes more noticeable. This is believed to be due to making too much zinc ion available.

SUMMARY OF THE INVENTION

The present invention relates to an oral composition comprising, in an orally acceptable carrier, from about 0.1% to about 5% zinc oxide; and from about 0.1% to about 5% of a source of carbonate ions selected from alkali metal and ammonium carbonates and bicarbonates. The molar ratio of carbonate ion to zinc ion is from 0.05:1 to 1:1. The composition has good anti-plaque efficacy and taste. Preferred compositions are toothpastes.

DETAILED DESCRIPTION OF THE INVENTION

Unless specified otherwise, all percentages and ratios herein are by weight of the total composition and all measurements are made at 25° C.

The oral compositions herein can take the form of dentifrice, leave-on oral gels, mouth rinses, candies, lozenges and chewing gums. The preferred forms are toothpastes, mouth rinses and leave-on oral gels, especially toothpastes.

The term "orally acceptable carrier" as used herein includes any safe and effective materials for use in the compositions of the present invention. Such materials include conventional additives in oral care compositions including but not limited to fluoride ion sources, anti-calculus or anti-tartar agents, desensitizing agents, teeth whitening agents such as peroxide sources, abrasives such as silica, herbal agents, chelating agents, buffers, anti-staining agents, alkali metal bicarbonate salts, thickening materials, humectants, water, surfactants, a flavour system, sweetening agents, colouring agents, and mixtures thereof.

The term "dentifrice", as used herein, means a substance for cleaning the teeth which is suitable for application with a toothbrush and is rinsed off after use. It can be a powder, paste, gel, or liquid formulation unless otherwise specified.

Dentifrice compositions herein can be single, dual or multi phase preparations. A single phase may comprise a liquid carrier with one or more insoluble particles, such as of a dental abrasive, homogeneously or evenly dispersed within it.

Leave-on oral gels are products which are intended for application to the teeth or gums and, though being intended only for temporary application, as distinct from dental filling materials or permanent dental coatings, are not rinsed off shortly after application, other than by the normal action of saliva. They may be applied locally or spread around the teeth or gums, such as those products described in WO 2004/017933, which are intended for overnight usage. By "mouth washes" or "mouth rinses" is meant those liquid products which are imbibed or sprayed into the mouth, sluiced around the mouth and then expectorated.

The compositions herein comprise an anti-plaque effective amount of zinc oxide particles. Zinc oxide is an especially useful source of zinc for oral compositions because it provides a weight efficient way of incorporating zinc and it can be manufactured cheaply at high purity. Since it is relatively insoluble it does not, in the absence of other ingredients, give rise to a strong, objectionable taste. However, its low inherent solubility does not lend itself to high anti-plaque activity. It has been found though that, through proper formulation of the rest of the composition, good anti-plaque efficacy can be obtained from levels of zinc oxide of from about 0.1% to about 5%, preferably from about 0.4% to about 1.2% by weight.

The zinc oxide particles preferably have a mean particle size of from about 0.05 to about 0.5 micron.

A further essential feature of the invention herein is a source of carbonate ions selected from alkali metal and ammonium carbonates and bicarbonates. Preferred are the alkali metal carbonates and bicarbonates, more preferably sodium carbonate and potassium carbonate, and most especially potassium carbonate since this has been found to give a further improvement in palatability of the composition relative to use of the sodium salt.

Though it is preferable for the anti-plaque efficacy of the composition to have a carbonate ion source present, as discussed above it has been found that with too much carbonate present the objectionable zinc taste can re-appear. It is preferable therefore for there to be a further limitation on the amount of carbonate relative to the zinc. In general the molar ratio of carbonate ion to zinc ion should be within the range of from about 0.05:1 to about 1:1, preferably from about 0.1:1 to about 0.7:1 and especially within the range from about 0.15:1 to about 0.45:1. The carbonate ion source may be either fully or partially dissolved in the composition or may be in the form of suspended particles.

The pH of the compositions herein will generally range from about 6 to about 9.5, more preferably from about 7.5 to about 8.5. The pH of a dentifrice composition is measured from a 3:1 aqueous slurry of the dentifrice, i.e., 3 parts water to 1 part dentifrice.

Orally Acceptable Carrier Materials

The orally acceptable carrier comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy.

The carriers or excipients of the present invention can include the usual and conventional components of dentifrices, non-abrasive gels, subgingival gels, mouthwashes or rinses, mouth sprays, chewing gums, lozenges and breath mints as more fully described hereinafter.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849, 213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910, issued Mar. 30, 1993 and Sep. 7, 1993, respectively both to Damani. Carriers suitable for the preparation of compositions of the present invention are well known in the art. Their selection will depend on secondary considerations like taste, cost, and shelf stability, etc.

The compositions of the present invention may be in the form of leave-on oral gels, which may be aqueous or non-aqueous. Aqueous gels generally include a thickening agent (from about 0.1% to about 20%), a humectant (from about 10% to about 55%), flavour, sweeteners and colour as desired and the balance water. The compositions may comprise an anticarries agent (from about 0.05% to about 0.3% as fluoride ion), and an anticalculus agent (from about 0.1% to about 13%).

In a preferred embodiment, the compositions of the subject invention are in the form of dentifrices, such as toothpastes, tooth gels and tooth powders. Components of such toothpaste and tooth gels generally include one or more of a dental abrasive (from about 6% to about 50%), a surfactant (from about 0.1% to about 2.5%), a thickening agent (from about 0.1% to about 5%), a humectant (from about 15% to about 45%), a flavouring agent (from about 0.04% to about 2%), a sweetening agent (from about 0.1% to about 3%), a colouring agent (from about 0.01% to about 0.5%) and water (from about 2% to about 45%). Such toothpaste or tooth gel may also include one or more of an anticarries agent (from about 0.05% to about 0.3% as fluoride ion) and an anticalculus agent (from about 0.1% to about 13%). Tooth powders, of course, contain substantially all non-liquid components.

Other embodiments of the subject invention are mouthwashes or rinses and mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavouring agent (from about 0.04% to about 2%), a sweetening agent (from about 0.1% to about 3%), and a colouring agent (from about 0.001% to about 0.5%). Such mouthwashes and mouth sprays may also include one or more of an anticarries agent (from about 0.05% to about 0.3% as fluoride ion) and an anticalculus agent (from about 0.1% to about 3%).

The compositions of the subject invention may also be in the form of dental solutions and irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and compressed tablets. The term "fast-dissolving solid form" as used herein means that the solid dosage form dissolves in less than about 60 seconds, preferably less than about 15 seconds, after placing the solid dosage form in the oral cavity. Fast-dissolving solid forms are disclosed in commonly-assigned WO 95/33446 and WO 95/11671; U.S. Pat. No. 4,642,903; U.S. Pat. No. 4,946,684; U.S. Pat. No. 4,305,502; U.S. Pat. No. 4,371,516; U.S. Pat. No. 5,188,825; U.S. Pat. No. 5,215,756; U.S. Pat. No. 5,298,261; U.S. Pat. No. 4,687,662.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: *The Science and Practice of Pharmacy*, 19$^{th}$ Ed., Vol. II, Chapter 92, 1995. Lozenge compositions (compressed tablet type) typically include one or more fillers (compressible sugar), flavouring agents, and lubricants. Microcapsules of the type contemplated herein are disclosed in U.S. Pat. No. 5,370,864, Peterson et al., issued Dec. 6, 1994.

In still another aspect, the invention provides a dental implement impregnated with the present composition. The dental implement comprises an implement for contact with teeth and other tissues in the oral cavity, said implement being impregnated with the present composition. The dental implement can be impregnated fibers including dental floss or tape, chips, strips, films and polymer fibers.

Types of orally acceptable carriers or excipients which may be included in compositions of the present invention, along with specific non-limiting examples, are discussed in the following paragraphs.

Water is commonly used as a carrier material in oral compositions. It is useful as a processing aid, is benign to the mouth and it assists in quick foaming of toothpastes. Water may be added as an ingredient in its own right or it may be present as a carrier in other common raw materials such as sorbitol and sodium lauryl sulphate. The term 'total water' as used herein means the total amount of water present in the composition, whether added separately or as a solvent or carrier for other raw materials but excluding that may be present as water of crystallisation in certain inorganic salts. The amount of water present will typically depend upon the particular form of the composition and may vary widely. Preferred toothpaste compositions herein comprise from about 20% to about 65%, more preferably about 30% to about 55% total water.

An optional but preferred component of the compositions herein is a humectant. The humectant serves to keep the dentifrice from hardening upon exposure to air, to give a moist feel to the mouth, and, for particular humectants, to impart a desirable sweetness of flavour. The humectant, on a pure humectant basis, generally comprises from about 5% to about 70%, preferably from about 15% to about 45%, by weight of the composition. Suitable humectants include edible polyhydric alcohols such as glycerin, sorbitol, xylitol, butylene glycol, polyethylene glycol, and propylene glycol, especially sorbitol and glycerin.

Dentifrice compositions of the present invention will generally include a surfactant. Useful surfactant types include anionic, nonionic, cationic and betaine surfactants. Anionic surfactants can be included to provide cleaning and foaming properties, and are typically used in an amount from about 0.1% to about 2.5%, preferably from about 0.3% to about 2.5% and most preferably from about 0.5% to about 2.0% by weight. Cationic surfactants can also be used though care needs to be taken over their compatibility with other ingredients. They would typically be used at levels similar to those of the additional anionic surfactants, as would betaine surfactants. Some nonionic surfactants may be useful at substantially higher levels, such as up to about 20% if it is desired to use them to form a ringing gel.

Anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Also useful herein are sarcosinate surfactants, isethionate surfactants and taurate surfactants, such as lauroyl sarcosinate, myristoyl sarcosinate, palmitoyl sarcosinate, stearoyl sarcosinate and oleoyl sarcosinate. All of the foregoing are generally used as their alkali metal or ammonium salts.

It has further been found that certain alkyl sulfoacetate surfactants such as sodium lauryl sulfoacetate and diethylhexyl sodium sulfoacetate can also be effective in reducing the astringency of zinc containing compositions. The sulfoacetates can be used for this purpose in addition to other anionic surfactants.

Examples of suitable nonionic surfactants include the poloxamers, polyethylene oxide condensates of alkyl phenols, long chain tertiary amine oxides, long chain tertiary phosphine oxides, long chain dialkyl sulfoxides and mixtures of such materials. Preferred betaine surfactants include cocoamidoethyl betaine, cocoamidopropyl betaine, lauramidopropyl betaine and the like.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; cetyl pyridinium fluoride; etc. Some of these cationic surfactants are also useful as anti-microbial agents.

In preparing toothpaste or gels, it is often necessary to add a thickening agent or binder to provide a desirable consistency of the composition, to provide desirable active release characteristics upon use, to provide shelf stability, and to provide stability of the composition, etc. Thickening agents can include carboxyvinyl polymers, carrageenan, nonionic cellulose derivatives such as hydroxyethyl cellulose, and water soluble salts of cellulose derivatives such as sodium carboxymethylcellulose. It should be recognised though that the anionic polymers such as carboxyvinyl polymers can interact with zinc ions in a way which reduces the effectiveness of the zinc and the interaction may also have an undesirable effect on the rheology of the composition. Natural gums such as gum karaya, xanthan gum, gum arabic, and gum tragacanth can also be used herein. Xanthan gum is preferred. Also preferred is a thickener system comprising a mixture of xanthan gum and hydroxyethyl cellulose, which can provide a thickened composition without stringiness. Suitable thickening agent levels can range from about 0.1 to about 5%, and higher if necessary.

A preferred ingredient herein for a dentifrice, more especially a toothpaste, is a dental abrasive. Abrasives serve to polish the teeth and/or remove surface deposits. The abrasive material contemplated for use herein can be any material which does not excessively abrade dentine. Suitable abrasives include insoluble phosphate polishing agents, include various calcium phosphates such as, for example, dicalcium phosphate, tricalcium phosphate, calcium pyrophosphate, beta-phase calcium pyrophosphate, dicalcium phosphate dihydrate, anhydrous calcium phosphate, insoluble sodium metaphosphate, and the like. Also suitable are chalk-type abrasives such as calcium and magnesium carbonates, silicas including xerogels, hydrogels, aerogels and precipitates, alumina and hydrates thereof such as alpha alumina trihydrate, aluminosilicates such as calcined aluminium silicate and aluminium silicate, magnesium and zirconium silicates such as magnesium trisilicate and thermosetting polymerised resins such as particulate condensation products of urea and formaldehyde, polymethylmethacrylate, powdered polyethylene and others such as disclosed in U.S. Pat. No. 3,070,510, Dec. 25, 1962. Mixtures of abrasives can also be used. Silica dental abrasives of various types are preferred because of their unique benefits of exceptional dental cleaning and polishing performance without unduly abrading tooth enamel or dentine. The abrasive polishing materials generally have an average particle size of from about 0.1 to about 30 microns, preferably from about 5 to about 15 microns.

The total amount of abrasive in dentifrice compositions of the subject invention typically range from about 6% to about 70% by weight; toothpastes preferably contain from about 10% to about 50% of abrasives, by weight of the composition. Dental solution, mouth spray, mouthwash and non-abrasive gel compositions of the subject invention typically contain little or no abrasive.

Another preferred ingredient is a water-soluble fluoride compound, used in an amount sufficient to give a fluoride ion concentration in the composition of from about 0.05% to about 0.5% by weight, to provide anti-caries effectiveness. A wide variety of fluoride ion-yielding materials can be employed as sources of soluble fluoride in the present compositions. Representative fluoride ion sources include stannous fluoride, sodium fluoride, potassium fluoride, sodium monofluorophosphate and many others. Stannous fluoride and sodium fluoride are particularly preferred, as well as mixtures thereof. If, however, sodium fluoride is used in combination with the long chain polyphosphates then it is preferably kept in a separate phase.

Another optional component of the present compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

Other antimicrobial agents may also be employed. Included among such agents are water insoluble non-cationic antimicrobial agents such as halogenated diphenyl ethers, particularly triclosan and essential oils such as thymol. Water soluble antimicrobials include quaternary ammonium salts such as cetyl pyridinium chloride. Enzymes are another type of active that may be used in the present compositions. Useful enzymes include those that belong to the category of proteases, lytic enzymes, plaque matrix inhibitors and oxidases. The oxidases also have whitening/cleaning activity, in addition to anti-microbial properties. Such agents are disclosed in U.S. Pat. No. 2,946,725, Jul. 26, 1960, to Norris et al. and in U.S. Pat. No. 4,051,234, Sep. 27, 1977 to Gieske et al.

Another preferred optional agent is an anticalculus agent, such as a soluble polyphosphate, polyphosphonate or pyrophosphate. The pyrophosphates used in the present compositions can be any of the alkali metal pyrophosphate salts. Specific salts include tetra alkali metal pyrophosphates, dialkali metal diacid pyrophosphates, trialkali metal monoacid pyrophosphates and mixtures thereof, wherein the alkali metals are preferably sodium or potassium. The salts are useful in both their hydrated and unhydrated forms. An effective amount of pyrophosphate salt useful in the present composition is generally enough to provide at least about 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7^{-4}$ (e.g., $(HP_2O_7^{-3})$) may be present when a final product pH is established. The pyrophosphate salts are described in more detail in Kirk & Othmer, Encyclopedia of Chemical Technology, Third Edition, Volume 17, Wiley-Interscience Publishers (1982). Also useful are the soluble polyphosphates such as sodium tripolyphosphate and sodium hexametaphosphate. Other long chain anticalculus agents of this type are described in WO 98/22079. Particularly preferred for use herein are sodium polyphosphate salts containing about 15 to about 25 phosphate units.

Flavouring and sweetening agents are preferably also included in the present compositions. It is an advantage of the present invention that a wide range of flavouring ingredients can be used. Suitable flavouring agents and sweetening agents are well known in the art. Suitable flavour levels in the present oral compositions herein are from 0.1% to 5.0%, more preferably from 0.5% to 2.0%, and most preferably from about 0.7% to about 1.8%, by weight. Typically, a flavour oil will be manufactured in a separate step and will comprise multiple components, natural and/or synthetic in origin, in order to provide a balanced flavour which is acceptable to a broad range of people. Flavour components can be selected from mint, spice, fruit, citrus, herbal, medicinal, and common food flavour types (e.g. chocolate). Illustrative, but non-limiting examples of such components include hydrocarbons such as limonene, caryophyllene, myrcene, and humulene; alcohols such as menthol, linalool, 3-decanol, and pinocarveol; ketones such as piperitone, menthone, spicatone, and 1-carvone; aldehydes such as acetaldehyde, 3-hexanal, or n-octanal; oxides such as menthofuran, piperitone oxide, or carvyl acetate-7,7 oxide; acids such as acetic and ocenoic; and sulphides such as dimethyl sulphide. Components also include esters such as menthyl acetate, benzyl isobutyrate, and 3-octyl acetate. The flavour components may also include essential oils such as peppermint oils from e.g., Mentha piperita and Mentha arvensis; spearmint oils such as those from Mentha cardiaca and Mentha spicata; sage oil, parsley oil, marjoram oil, cassia oil, clove bud oil, cinnamon oil, orange oil, lime oil, eucalyptus oil and anise oil. Other suitable components are cinnamic aldehyde, eugenol, ionone, anethole, eucalyptol, thymol, methyl salicylate, vanillin, ethyl vanillin, and vanilla extracts. Whilst it is an advantage of the present invention that it provides for greater flexibility in flavour selection, those flavouring systems described in the art as being particularly suitable for zinc formulae, such as those described in U.S. Pat. No. 6,306,372 and WO 00/28952, can of course be used. Flavour components are described in more detail in Fenaroli's Handbook of Flavor Ingredients, Third Edition, Volumes 1 & 2, CRC Press, Inc. (1995), and Steffen Arctander's Perfume and Flavour Chemicals, Volumes 1 & 2, (1969). A physiological cooling agent can also be incorporated into the flavour oil. The coolant can be any of a wide variety of materials. Included among such materials are carboxamides, menthol, acetals, ketals, diols, and mixtures thereof. Preferred coolants herein include the p-menthane carboxamide agents such as N-ethyl-p-menthane-3-carboxamide, (known commercially as "WS-3") and mixtures thereof and menthone glycerine acetal (known commercially as "MGA"). Further coolants suitable for the present invention are disclosed in WO97/06695.

The compositions herein can further include herbal ingredients such as extracts of chamomile, oak bark, melissa, rosemary and salvia. These, and some of the herb-derived flavouring components mentioned above (such as thymol) can be included at levels just sufficient to provide a contribution to the flavour or they can be added at higher levels, such as 1% or more, in order to provide a greater therapeutic effect.

Sweetening agents which can be used include sucrose, glucose, saccharin, sucralose, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate, sucralose and sodium saccharin, and mixtures thereof. A composition preferably contains from about 0.1% to about 3% of these agents, more preferably from about 0.1% to about 1%.

The compositions may further include usual pigments, dyes and opacifiers, such as titanium dioxide.

It will be appreciated that when selecting components from the list above, the components chosen must be chemically and physically compatible with one another.

The nature of the present invention will be understood with reference to the following non-limiting Examples.

Examples 1-3 illustrate toothpaste examples according to the invention

|  | 1 % | 2 % | 3 % |
| --- | --- | --- | --- |
| Water purified | 37.43 | 31.11 | 38.13 |
| Zinc oxide (USP 1) | 1.20 | 0.80 | 0.80 |
| Sodium fluoride | 0.32 | 0.32 | 0.32 |
| Sodium saccharin | 0.30 | 0.45 | 0.30 |
| Sorbitol (70%) | 31.00 | 31.00 | 31.00 |
| Glycerin | 4.75 | 4.75 | 4.75 |
| Hydrated silica amorphous | 15.00 | 21.00 | 15.00 |
| Natrosol 250M (Hydroxyethyl cellulose) | 0.50 | 1.35 | 0.50 |
| Xanthan Gum (Keltrol 1000) | 1.00 | 0.70 | 1.00 |
| Sodium Carbonate | 0.50 | 0 | 0.40 |
| Potassium Carbonate | 0 | 0.52 | 0 |
| Sodium lauryl sulphate 28% | 7.00 | 7.00 | 7.00 |
| Flavour | 1.00 | 1.00 | 0.80 |
| Total | 100.00 | 100.00 | 100.00 |
| Molar ratio of carbonate (ion) to zinc | 0.32 | 0.38 | 0.38 |

Zinc oxide was added to the purified water and dispersed. Sodium fluoride and sodium saccharin were dissolved in the dispersion with thorough mixing and then with thorough mixing under vacuum, the following sets of ingredients were added in turn: (i) sorbitol and glycerine; (ii) hydrated amorphous silica, xanthan gum, hydroxyethyl cellulose, and sodium carbonate—mixing being continued until a smooth paste was formed; (iii) sodium lauryl sulphate and flavour oils.

Example 4 is a mouth rinse formulation according to the invention. The molar ratio of carbonate (ion) to zinc is 0.32.

|  | % |
| --- | --- |
| Purified water | q.s. |
| Ethanol 96% EP | 9.23 |
| Glycerin | 23.00 |
| Flavour | 0.13 |
| Natrosol 250M | 0.05 |
| Saccharin | 0.02 |
| Colour | 0.0008 |
| Citric acid anhydrous | 0.00022 |
| Sodium benzoate | 0.00010 |
| Potassium sorbate | 0.00010 |
| Zinc oxide | 0.12 |
| Sodium carbonate | 0.05 |

The mouth rinse is prepared as follows:

To the purified water (~5% of total) add sthe odium benzoate, potassium sorbate, citric acid, and colours. Mix thoroughly and dissolve to form a dye pre-mix.

Mix together water (~55% of total) ethanol and glycerine and then add the Natrosol 250M (hydroxyethyl cellulose), flavour, sodium carbonate and sodium saccharin. Mix thoroughly until the solids are all dissolved. Add the dye-premix, and zinc oxide. Add the remaining water (~40% of total) and mix thoroughly.

Example 5 is a chewing gum formulation according to the invention. It has a molar ratio of carbonate (ion) to zinc of 0.25 and is prepared as follows:

Heat the gum base to its softening point 57° C. (±5°), ensuring that the temperature is kept below 70° C. Add the sorbitol, xylitol, lycasin, mannitol, glycerine, zinc oxide, potassium carbonate, titanium dioxide, flavour, menthol, sucralose, Acesulfame K and sodium hexametaphosphate.

Mix all the ingredients with a suitable blade mixer, maintaining a temperature in the range 44-48° C. Roll the gum core to the correct thickness and cut into pieces. The gum core is then dried, coated, dried and finally waxed. It should be stored in a dry air-tight container.

| Ingredient | % |
| --- | --- |
| Sorbitol | 13.5 |
| Nova gum base | 36.5 |
| Xylitol | 20 |
| Lycasin | 6 |
| Mannitol | 1.5 |
| Zinc Oxide | 1.2 |
| Potassium carbonate | 0.5 |
| Glycerine | 6 |
| Titanium Dioxide | 0.15 |
| Sodium hexametaphosphate (Glass H)[1] | 7.5 |
| Flavour | 6.5 |
| Menthol SD | 0.5 |
| Sucralose | 0.07 |
| Acesulfame K | 0.08 |

[1] A linear polyphosphate manufactured by FMC Corporation having an average PO3 chain length of ~21.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral composition comprising:
   a) from about 0.1% to about 5% zinc oxide insoluble particles as essential anti-plaque agent;
   b) a source of carbonate ions selected from alkali metal and ammonium carbonates; and
   c) an orally acceptable carrier including water;
   wherein the composition has a molar ratio of carbonate ion to zinc ion of from about 0.05:1 to about 0.45:1 to provide sufficient bioavailable zinc for anti-plaque efficacy with acceptable aesthetics.

2. An oral composition according to claim 1 in the form of an aqueous toothpaste having a pH of from about 6 to about 9.5.

3. An oral composition according to claim 1 wherein the source of carbonate ions is selected from sodium carbonate and potassium carbonate.

4. An oral composition according to claim 3 wherein the source of carbonate ions is potassium carbonate.

5. An oral composition according to claim 1 comprising from about 0.4 to about 1.2% by weight of zinc oxide.

6. An oral composition according to claim 1 wherein the molar ratio of carbonate ion to zinc ion is from about 0.15:1 to about 0.45:1.

7. An oral composition according to claim 2 wherein the composition has a pH of from about 7.5 to about 8.5.

8. An oral composition according to claim 6 which is in the form of a toothpaste and comprises from about 20% to about 65% total water.

9. An oral composition according to claim 8 comprising from about 30% to about 55% total water.

10. An oral composition in the form of a toothpaste comprising:
    a) from about 0.4% to about 1.2% zinc oxide insoluble particles as essential anti-plaque agent;
    b) a source of carbonate ions selected from alkali metal and ammonium carbonates; and
    c) an orally acceptable carrier including from about 20% to about 65% total water by weight of the oral composition;
    wherein the composition has a molar ratio of carbonate ion to zinc ion of from about 0.15:1 to about 0.45:1 to provide sufficient bioavailable zinc for anti-plaque efficacy with acceptable aesthetics.

* * * * *